United States Patent [19]

Faubl et al.

[11] Patent Number: 4,640,910

[45] Date of Patent: Feb. 3, 1987

[54] ERYTHROMYCIN A SILYLATED COMPOUNDS AND METHOD OF USE

[75] Inventors: Hermann Faubl, Libertyville, Ill.; Robert G. Stein, Kenosha, Wis.

[73] Assignee: Abbott Laboratories, North Chicago, Ill.

[21] Appl. No.: 796,818

[22] Filed: Nov. 12, 1985

[51] Int. Cl.$^4$ ................. A61K 31/71; C07H 17/08
[52] U.S. Cl. .................................. 514/29; 536/7.2
[58] Field of Search .......................... 536/7.2; 514/29

[56] References Cited

U.S. PATENT DOCUMENTS 2,746,956  5/1956  Speier ................................ 536/7.2
4,382,085  5/1983  Sciavolino et al. ................ 514/29
4,382,086  5/1983  Sciavolino et al. ................ 536/7.2

*Primary Examiner*—Johnnie R. Brown
*Attorney, Agent, or Firm*—Martin L. Katz; Michael J. Roth

[57] ABSTRACT

Novel O-alkylsilyl derivatives of macrolide antibiotics are disclosed. These compounds have markedly superior taste properties when compared to the corresponding parent compounds.

8 Claims, No Drawings

ERYTHROMYCIN A SILYLATED COMPOUNDS AND METHOD OF USE

TECHNICAL FIELD

This invention relates to antibiotics for use in the chemotherapy of antimicrobial infections, and more particularly to derivatives of erythromycin antibiotics which exhibit superior taste properties which render them especially useful for oral dosage forms.

BACKGROUND ART

Common dosage forms for antibiotic drugs are oral solutions, suspensions, syrups, emulsions, and other liquids. Such dosage forms are particularly important at the extremes of age, i.e. in children and the elderly, who cannot easily swallow pills, tablets, capsules or other solid dosage forms. Unfortunately, many antibiotics which are frequently prescribed, as well as many new antibiotics under development, have a bitter taste to a greater or lesser degree. This bitterness can sometimes be eliminated by use of a salt or ester of the antibiotic, or the bitterness may be overcome by the use of flavorants and/or masking agents in the liquid vehicle of the dosage form. In the case of some antibiotics in the the erythromycin or macrolide category, this bitterness is so pronounced that the usual means of eliminating or masking the undesirable taste are unable to provide a palatable dosage form. As a result, there is a continuing need for novel derivatives of these compounds which are flavorless or which have a much reduced bitter taste.

Creamer, *Pharmaceutical Technology*, 6(3) (March, 1982), "Organosilicon Chemistry and Its Application in the Manufacture of Pharmaceuticals", printed by the Silicones and Urethane Intermediates Division of Union Carbide Corporation and identified as SUI-185 5/82-2M, describes the use of silylation in producing various drugs and drug intermediates. A detailed bibliography is also provided.

U.S. Pat. No. 2,746,956, "Method of Silylating Organic Comopounds" describes what is claimed to be the synthesis of a silylated erythromycin derivative. The patentee states that a bis-silylated compound was obtained. However, the experimental method of the '956 patent has been repeated and found not to provide the results indicated.

It is an object of this invention to provide novel macrolide antibiotic compounds.

It is another object of this invention to provide antibiotic compounds which are sufficiently flavorless to be used in liquid dosage forms for oral administration.

These and other objects of the invention will be evident from the following disclosure.

DISCLOSURE OF THE INVENTION

This invention provides relatively acid stable macrolide antibiotics in which one or more of the hydroxyl groups are replaced by a group of the formula —O—SiR'R''R''', where R', R'', and R''' are hydrogen or $C_1$ to $C_8$ alkyl, cycloalkyl, alkaryl or alkenyl, provided that at least one of R', R'', and R''' is not hydrogen; and pharmaceutically acceptable salts and esters thereof.

In the preferred embodiments, this invention provides compounds of the formulas

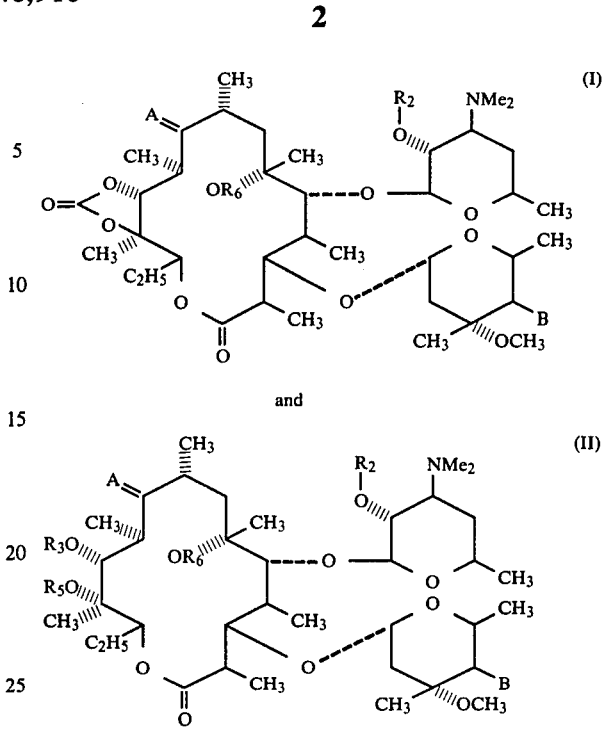

where A is =O or =N—$OR_1$, and B is H or $OR_4$, where $R_1$, $R_2$, $R_3$, $R_4$ and $R_5$ are independently selected from hydrogen, $C_1$ to $C_8$ alkyl and SiR'R''R''', where R', R'', and R''' are hydrogen or $C_1$ to $C_8$ alkyl, substituted alkyl, cycloalkyl, alkyl or alkenyl, provided that R', R'', and R''' are not all hydrogen; and $R_6$ is selected from hydrogen, methyl, and ethyl;

provided that at least one of $R_1$-$R_5$ is of the formula SiR'R''R''', as defined above, and further provided that when A is =O and B is H, at least one of $R_1$ to $R_6$ is neither hydrogen nor SiR'R''R'''. Preferred are compounds of formula (I) wherein $R_2$ is trimethylsilyl, A is =O, $R_6$ is hydrogen, and B is H or $OR_4$ where $R_4$ is $C_1$ to $C_8$ alkyl; and compounds of formula (II) wherein A is =O, $R_2$ is trimethylsilyl, B is OH, and $R_6$ is methyl. Especially preferred is the compound of formula (II) where A=O, $R_2$ is trimethylsilyl, B is $OR_4$, $R_3$-$R_5$ are all hydrogen, and $R_6$ is methyl, i.e., 2'-trimethylsilyl-6-O-methyl erythromycin A.

The terms "alkyl", "cycloalkyl" and "alkenyl" are used herein to mean straight and branched chain saturated, cyclic and unsaturated radicals, respectively, including, but not limited to, methyl, ethyl, ethenyl, n-propyl, isopropyl, 2-propenyl, n-butyl, sec-butyl, isobutyl, tert-butyl, 1-, 2-, or 3-butenyl, cyclopropyl, cyclohexyl, ethylcyclohexyl, and the like.

By "substituted alkyl" is meant alkyl groups as defined above but in which one or more hydrogen atoms is replaced by a heteroatomic functional group such as amino, imino, halo, alkoxy, nitro, acetoxy, acetamido, hydroxy, cyano, and the like.

By "alkaryl" herein is meant a substituted or unsubstituted aromatic ring group appended to an alkyl radical as defined above, including, but not limited to benzyl, halobenzyl, nitrobenzyl, alkylbenzyl, alkoxybenzyl, phenethyl and the like.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

By "relatively acid stable" is meant significantly more stable, as determined by standard statistical criteria, than erythromycin A base in water at a pH less than 3.

The compounds of the present invention can be used in the form of salts derived from inorganic or organic acids. Among the more commonly used salts and esters of erythromycin antibiotics are the estolate (propionate lauryl sulfate salt), ethyl succinate, gluceptate (glucoheptonate), lactobionate, stearate, and hydrochloride forms. Other acid salts used in the pharmaceutical arts are the following: acetate, adipate, alginate, aspartate, benzoate, benzenesulfonate, bisulfate, butyrate, citrate, camphorate, camphorsulfonate, cyclopentanepropionate, digluconate, dodecyl sulfate, ethanesulfonate, fumarate, gluconate, glycero-phosphate, hemisulfate, heptanoate, hexanoate, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Although quaternized macrolide antibiotics are, in general, drastically less active than the parent compound in-vivo, basic nitrogen-containing groups can be quaternized with such agents as lower alkyl halides, such as methyl, ethyl, propyl and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

While not intending to be limited by theory, it is believed that the silylated compounds of this invention function as pro-drugs, i.e., that the silyl group is cleaved and converted to yield the active parent antibiotic compound in the body. In this context, the particular importance of the preferred compounds of this invention will be appreciated. It has been determined that the compounds of this invention exhibit good aqueous stability at near-neutral pH (4–8), as is obtained in common oral dosage forms. However, in order for the silyl group or groups to be cleaved in vivo, an acid environment, such as that found in the stomach, is desirable. Thus, these compounds particularly lend themselves to oral dosage applications. At the same time, the preferred compounds of this invention, such as the 6-O-methyl erythromycin derivative, the erythromycin 11,12-carbonate derivatives, and others, are much more resistant to acidic conditions than erythromycin itself, which is well known to be rapidly degraded to inactive compounds under acidic conditions. As a result, the preferred compounds of this invention are activated rather than inactivated under acidic conditions, and provide, in effect, an intramolecular synergy between their palatability and pro-drug pharmacology one one hand, and their acid resistance on the other.

This invention also provides methods of treating and preventing infection by susceptible organisms in a human or lower animal host in need of such treatment, which method comprises administration to the human or lower animal host a therapeutically effective amount of a compound of this invention. The compounds of the present invention may be administered orally in dosage unit formulations containing conventional nontoxic pharmaceutically acceptable carriers, adjuvants and vehicles as desired.

Total daily dose of the compounds of this invention administered to a host in single or divided doses may be in amounts, for example, from 0.001 to 100 mg/kg body weight daily and more usually 0.5 to 15 mg. Dosage unit compositions may contain such amounts or submultiples thereof to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

These compounds can be used in any pharmaceutical composition commonly used for formulation of antibiotic dosage forms. Accordingly, this invention provides pharmaceutical compositions in unit dosage form, comprising a therapeutically effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, sesame oil, olive oil, safflower oil, corn oil and soybean oil; polyols such as propylene glycol, glycerin, sorbitol, mannitol and polyethylene glycol; esters such as ethyl oleate and ethyl laurate; agar; buffering agents such as calcium carbonate, magnesium hydroxide and aluminum hydroxide; alginic acid; pyrogen-free water; isotonic saline; Ringer's solution, ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration employed.

Solid dosage forms for oral administration may include capsules, tablets, pills, powders, prills and granules. In such solid dosage forms, the active compound may if desired be admixed with one or more inert diluents such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric or other release-controlling coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The term "administration" of the antibiotic or composition herein includes systemic use, as by oral administration thereof, as well as topical application of the compounds and compositions to the site of infection or potential infection.

By "a therapeutically effective amount" of the erythromycin antibiotic herein is meant a sufficient amount of the antibiotic compound to treat or prevent susceptible bacterial or other microbial infections, at a reasonable benefit/risk ratio applicable to any medical treatment. Of course, the total daily dosage of the compositions herein will be decided by the attending physician within the scope of sound medical judgment. The effective amount of the antibiotic of this invention will vary with the particular organism being treated, the severity of the infection, the duration of the treatment, the specific compound, ester or salt employed, the age and weight of the patient and like factors well known in the medical arts. In general, treatment regimens according to the present invention comprise administration to a patient in need of such treatment from about 100 milligrams to about 5,000 milligrams (preferably 500 to 2,000 milligrams) of the erythromycin compound of this invention per day in multiple doses or, preferably, in a single dose of from about 500 milligrams to about 1,000 milligrams.

The following examples illustrate the synthesis and use of the compounds and compositions of this invention.

EXAMPLE 1

2'-O-trimethylsilyl-4"-deoxy erythromycin A 11,12-carbonate

One gram of 4"-deoxy-erythromycin A-11,12-carbonate was dissolved in 10 mL of methylene chloride (MeCl$_2$) at room temperature, and the resulting solution was cooled for 25 minutes. At that point, the temperature of the solution was 9° C., and 0.34 g (0.47 mL) of triethylamine (Et$_3$N) was added, followed by 0.30 g (0.36 mL) of chlorotrimethylsilane (TMSCl). The resulting solution was clear and colorless. The reaction was left to stir at room temperature overnight (16 hours). The next day, the reaction mixture was light yellow in color, but clear. TLC analysis indicated a thorough conversion to a nonpolar product. The reaction mixture was washed with 150 mL of water, and the MeCl$_2$ layer was collected. This fraction was dried over MgSO$_4$ and evaporated at reduced pressure to yield 1.02 g (0.0012 mole, 96% yield) of 2'-O-trimethylsilyl-4"-deoxyerythromycin A 11,12-carbonate as a pale yellow foam.

Mass spectrum, m/z:M+ = 816.

EXAMPLE 2

2'-O-Trimethylsilyl Erythromycin A

To 70 mL of 1,2-dichloroethane (pre-dried over Na$_2$SO$_4$) was added 7.34 g erythromycin A and 2.1 mL triethylamine, followed by 1.6 mL of TMSCl. The reaction was monitored by TLC. After 5 hours, 1.6 mL more TMSCl and 2 mL Et$_3$N were added. After consumption of the starting material, the reaction was diluted with 50 mL water and 50 mL MeCl$_2$. The organic layer was washed with saturated aqueous NaHCO$_3$. Concentration of the MeCl$_2$ afforded 8.02 g of a foam. A small amount of this foam was dissolved in tetrahydrofuran and treated with (n-Bu)$_4$NF.3H$_2$O. According to TLC the product was reconverted to erythromycin A. 4.4 g of the above foam was recrystallized from hot hexane to afford 2.05 g of 2'-O-trimethylsilyl erythromycin A, m.p. 120°. Structure was confirmed by IR, NMR and mass spectra.

EXAMPLE 3

2'-O-trimethylsilyl-6-O-methyl-Erythromycin A

To 80 mL MeCl$_2$ was added 7.0 g 6-O-methyl erythromycin A and 2.8 mL Et$_3$N. The solution was cooled to 2° C. and 1.5 mL TMSCl was added. The solution was placed in a refrigerator. After 24 hours, an additional 0.9 mL Et$_3$N and 0.50 mL TMSCl was added. After two additional days, the reaction was diluted with 100 mL H$_2$O and 100 mL MeCl$_2$. The organic layer was washed with saturated aqueous NaHCO$_3$ and brine and dried over Na$_2$SO$_4$. After concentration and recrystallization from acetonitrile, 6.6 g of the 2'-O-trimethylsilyl (TMS) derivative was obtained, m.p. 157°–159°. Structure was confirmed by IR, NMR and mass spectra.

EXAMPLE 4

2',4",11-tris-(O-trimethylsilyl) Erythromycin A 7.34 g of erythromycin A were dissolved in 85 mL MeCl$_2$. The solution was treated with 12.2 mL Et$_3$N and 8.35 mL TMSCl. TLC monitoring indicated formation of spots of intermediate polarity and eventually a single spot of low polarity appeared. Workup similar to that used for preparation of 2'-O-TMS erythromycin A afforded 10.2 g of a foam. Recrystallization of 5.4 g of the foam from methanol-water (3:1) afforded a tacky powder. This was dissolved in heptane and dried with MgSO$_4$. Concentration afforded 3.44 g of the tris-O-TMS derivative, m.p. 120°–122°. Structure was confirmed by IR, NMR and mass spectra. In addition, reaction with (n-Bu)$_4$NF.3H$_2$O yielded erythromycin A according to TLC.

EXAMPLE 5

2'-Acetyl-4"-O-trimethylsilyl erythromycin A 11,12-carbonate 3.5 g of 2'-acetylerythromycin A 11,12-carbonate was reacted in MeCl$_2$ with Et$_3$N and TMSCl and worked up similar to the 2'-O-TMS-6-O-methyl erythromycin product of Example 3 to afford 4.01 g of a foam. Various recrystallization attempts failed and the remainder was finally concentrated to 2.8 g of a foam which was pure according to TLC. m.p. 125°–128°. Structure was confirmed by IR, NMR and mass spectra.

EXAMPLE 6

2',4"-diacetyl-11-O-TMS-Erythromycin A 1.79 g of 2',4"-diacetyl erythromycin A was reacted with Et$_3$N and TMSCl in MeCl$_2$ in the manner of Examples 1–5. Workup afforded 1.75 g of a powder, m.p. 113°–117°, whose spectra were consistent with 11-O-TMS-derivatization.

EXAMPLE 7

4"-O-trimethylsilyl erythromycin A-11,12-carbonate 2.11 g of 2'-acetyl-4"-O-TMS-erythromycin A 11,12-carbonate was stirred in 50 mL methanol and 0.36 g NaHCO$_3$. TLC showed clean conversion to a more polar material. The methanol was removed under vacuum, and the residue was partitioned between ethyl acetate and water. The EtOAc was washed with brine and dried over MgSO$_4$ and decolorizing carbon. Concentration of the filtrate afforded 1.90 g of the title compound, m.p. 127°–131°. Structure was confirmed by IR, NMR and mass spectra.

EXAMPLE 8

4''-O-trimethylsilyl erythromycin A 2.18 g of 2'-acetyl-4'',11-bis(O-trimethylsilyl) erythromycin A was stirred in 50 mL methanol containing 0.50 g NaHCO$_3$. After TLC showed disappearance of the starting material, the reaction mixture was concentrated to dryness and partitioned between water and hexane. The hexane was dried with MgSO$_4$ and concentrated to afford 1.94 g of a foam. Column chromatography (silica gel, 1:1:0.01 MeCl$_2$:CH$_3$CN:NH$_4$OH) led to the recovery of 900 mg of the title compound as a white foam, m.p. 116°–119°. Structure analyses by IR, NMR and mass spectroscopy confirmed that the 11-O-trimethylsilyl and 2'-acetate groups had been removed.

EXAMPLE 9

2'-acetyl-6-O-methyl-4'',11-bis-(O-TMS) Erythromycin A 0.98 g 2'-Acetyl-6-O-methyl erythromycin A was dissolved in 10 mL MeCl$_2$ and treated with 4.0 mL Et$_3$N and 3.2 mL TMSCl. TLC showed formation of what was presumed to be the mono-O-TMS compound. Eventually, a spot of a less polar product was formed. The reaction was partitioned between hexane and 1 N NaOH. The hexane was washed with brine, then dried over MgSO$_4$ and carbon. Concentration of the filtrate afforded 1.10 g of a foam, which was determined to be homogeneous by TLC. Structural analysis by IR, NMR and mass spectra confirmed that the title compound had been formed.

EXAMPLE 10

4''-11-bis(O-TMS)-6-O-methyl erythromycin A 0.56 g of 2'-acetyl-6-O-methyl-4''-11-bis (O-TMS) erythromycin A in 75 mL methanol was stirred at room temperature until all of the starting material was consumed. Evaporation of the MeOH afforded 0.50 g of a powder which was recrystallized from CH$_3$CN to afford 0.32 g of the title compound, m.p. 130°–132°. Spectra (IR, NMR) were consistent with the expected structure.

EXAMPLE 11

2',9-bis(O-trimethylsilyl)-Erythromycin A-9-oxime

A solution of 5.0 g erythromycin A 9-oxime in 200 mL MeCl$_2$ was distilled to half volume to remove traces of water. 5.1 mL of TMSCl and 6.1 mL of Et$_3$N were added. After one day another 5.1 mL of TMSCl and 6.1 mL of Et$_3$N were added. After the starting material was consumed, the reaction was concentrated and chromatographed (silica gel, 50:50:1 CH$_2$Cl$_2$:CH$_3$CN:NH$_4$OH) to afford 1.7 g of a light yellow solid whose mass and NMR spectra showed 2',9-bis-O-trimethylsilation.

EXAMPLE 12

2'-Acetyl-4'',11-bis (-O-TMS)-Erythromycin A 25 g of 2'-Acetyl Erythromycin A in 250 mL MeCl$_2$ was treated with 35 mL Et$_3$N and 25 mL TMSCl. After the starting material was consumed the reaction was partitioned between water and MeCl$_2$. The MeCl$_2$ layer was concentrated and chromatographed (silica gel, 100:100:1 MeCl$_2$:CH$_3$CN:NH$_4$OH) to afford 21 g of an off-white foam. A small portion was dissolved in tetrahydrofuran, treated with (n-Bu)$_4$NF.3H$_2$O, and its TLC showed reconversion to 2'-acetyl erythromycin A. The IR, MS and NMR spectra supported the assigned structure, as well as the subsequent conversions.

EXAMPLE 13

2'-O-Phenyldimethylsilyl-6-O-methyl erythromycin A

The title compound was prepared in the manner of Example 3 using 6-O-methyl erythromycin as the starting material and phenyldimethylsilyl chloride as the silylating reagent. As an added step, the 6-O-methyl erythromycin was dissolved in MeCl$_2$ and dried over MgSO$_4$ to remove any traces of water prior to adding the other reagents. The reaction proceeded smoothly. The isolated product was recrystallized from EtOAc-heptane to give crystals, m.p. 181–182. Structure was confirmed by IR and proton and carbon NMR spectra.

EXAMPLE 14

2',4'',9,11,12-pentakis(O-trimethylsilyl) erythromycin A-6,9-hemiketal 2.37 g of this compound was prepared from 1.70 g Erythromycin A according to the procedure of *Analyt. Chem.* 43 818 (1971), m.p. 95°–100°. Structure was confirmed by IR, NMR and mass spectra.

EXAMPLE 15

2'-(O-n-butyldimethylsilyl)-6-O-methyl erythromycin A 5.50 g of 6-O-methyl erythromycin A was treated with an excess of Et$_3$N and n-butyldimethylsilyl chloride in the manner of the foregoing examples at a temperature of 16°–20° C. The resulting crude solid was isolated and recrystallized from ethyl acetate-heptane to yield a first crop of 3.28 g of the title compound, m.p. 186°–189° C. On standing, the filtrate afforded a second crop of 0.60 g. Structure was confirmed by IR and NMR spectra.

EXAMPLE 16

2'-O-(3-Cyanopropyl) dimethylsilyl-6-O-methyl erythromycin A 14.3 g of 6-O-methyl erythromycin A was mixed with 160 mL ethyl acetate and 3.9 mL Et$_2$N. The slurry was cooled to 5° C. and treated with 9.10 g of (3-cyanopropyl)dimethylsilyl chloride and kept at 2° C. Over the next two days an additional 4 mL Et$_2$N and 4 g chlorosilane were added. The reaction was worked up on the second day by adding 50 mL water and washing the EtOAc layer with 80 mL 1 N NaOH and 80 mL brine. The EtOAc was dried with MgSO$_4$ and concentrated to afford 25.5 g of an oil which also contained the bis derivative and the side product from the chlorosilane. Column chromatography over 600 mL silica gel with a gradient of 3:1 EtOAc:hexane, 4:1 EtOAc:hexane, 5:1 EtOAc:hexane and pure EtOAc gave 9.3 g of substantially pure title compund, which was pooled with 3.8 g of similarly purified material from a different run. Recrystallization of the 13.1 g from 10:1 heptane:EtOAc afforded 5.5 g of the title compund, m.p. 176-177, whose infrared spectrum and carbon and proton NMR spectra supported the structure assignment.

EXAMPLE 17

2'-O-(3-cyanopropyl) dimethylsilyl erythromycin A

Erythromycin A (14.3g) was stirred in 250 mL MeCl$_2$ with 5.5 g MgSO$_4$, filtered and cooled to 2° C. Then 6.16 mL Et$_3$N and 6.23 g 3-cyanopropyl dimethylsilyl chloride were added and the solution was stored in a refrigerator. After two days an additional 3 mL Et$_3$N and 3 g silyl chloride were added. After two days more the reaction was cooled to $-15°$ C. and treated with 50 mL 1 N aqueous NaOH. The layers were separated and the McCl$_2$ was washed with brine and dried with MgSO$_4$ and concentrated. The 22.1 g of oil thus obtained showed the desired product, some bis derivative, and the side product from the silyl chloride. This oil was chromatographed on 1100 mL silica gel with a gradient of 3:1 EtOAc:hexane, EtOAc, and 4:1 EtOAc:MeOH. The fractions showing clean mono derivative were pooled and recrystallized from 7:1 heptane:EtOAc to afford 3.0 g of the title compound, m.p. 171-173. Spectral data supported the assigned structure.

The compounds of this invention can also be used as O-protected intermediates for the synthesis of other erythromycin derivatives, in well known synthetic techniques which require blocking groups for protection of the relatively labile hydroxyl substituents. When desired, the silyl protecting groups can be removed by treatment with an acidic medium, or by other techniques for removing silyl substituents, as taught in the art.

EXAMPLE 18

Following preliminary safety evaluations, the compounds of Examples 2 and 3 were suspended in water and sampled by four tasters experienced in evaluating the organoleptic acceptability of antibiotics. Each judged the compounds virtually tasteless. One taster reported a slight saline taste about two hours after tasting. Each of the four tasters also sampled suspensions of one parent compound, 6-O-methyl erythromycin A, in water and each judged the compound to be extremely bitter.

EXAMPLE 19

The antimicrobial spectrum of the 2'-O-TMS-6-O-methyl erythromycin A of this invention was determined by the following method:

Twelve petri dishes containing successive aqueous dilutions of the test compound mixed with 10 mL of sterilized Brain Heart Infusion agar (Difco 0418-01-5) are prepared. Each plate is inoculated with 1:100 (or 1:10 for Slow-growing strains, primarily Micrococcus and Streptococcus) dilutions of up to 32 different microorganisms, using a Steers replicator block. The inoculated plates are incubated at 35°-37° C. for 20-24 hours. In addition, a control plate, using BHI agar containing no test compound, is prepared and incubated at the beginning and end of each test.

An additional plate containing a compound having known susceptibility patterns for the organisms being tested and belonging to the same antibiotic class as the test compound is also prepared and incubated as a further control, as well as to provide test-to-test comparability. Erythromycin A was used for this purpose.

After incubation, each disk is read. The MIC is defined as the lowest concentration of drug yielding no growth, a slight haze, or sparsely isolated colonies on the inoculum spot as compared to the growth control.

The results are indicated in the following table.

TABLE 1

| Organism | MIC (ug/ml) | MIC-Std.* |
| --- | --- | --- |
| Staph. aureus ATCC 6538P | .78 | .2 |
| Staph. aureus CMX 686B | .78 | .2 |
| Staph. aureus A 5177 | 3.1 | .78 |
| Staph. aureus 45 | .78 | .1 |
| Staph. aureus 45 RAR2 | .78 | .2 |
| Staph. epidermidis 3519 | .78 | .2 |
| Staph. epidermidis 3519 RARI | .39 | .2 |
| Micrococcus luteus 9341 | .1 | .02 |
| Micrococcus luteus 4698 | .39 | .2 |
| Lactobacillus casei ATCC 7469 | .1 | .05 |
| Strep. faecium ATCC 8043 | .2 | .1 |
| Strep. bovis A5169 | .1 | .02 |
| Strep. agalactiae CMX 508 | .1 | .02 |
| Strep. pyogenes EES61 | .05 | .02 |
| Strep. pyogenes 930 | 100 | 100 |
| E. coli JUHL | 100 | 50 |
| E. coli SS | .39 | .2 |
| E. coli DC-2 | 100 | 100 |
| E. coli H560 | 100 | 25 |
| Enterobact. aerogenes ATCC 13048 | 100 | 100 |
| Klebsiella pneumoniae 8045 | 100 | 50 |
| Providencia stuartii CMX 640 | 100 | 100 |
| Ps. aeruginosa BMH10 | 100 | 100 |
| Ps. aeruginosa A5007 | 100 | 100 |
| Ps. aeruginosa K799/WT | 100 | 100 |
| Ps. aeruginosa K799/61 | 25 | 12.5 |
| Ps. cepacia 2961 | 100 | 100 |
| Acinetobacter sp. CMX 669 | 50 | 25 |

*Erythromycin A

EXAMPLE 20

Acute Mouse Protection Activity

The acute mouse protection test is conducted on ten mice with each of three levels of drug. Mouse mortality is used to calculate an ED50 value, i.e., the dose of drug required to protect 50% of the test animals against death due to the inoculum challenge.

The acute mouse protection test is conducted on female, Swiss albino mice, 18-20 grams in weight. The mice are injected intraperitoneally with an 18-hour culture of the indicated test organism diluted sufficiently to provide the desired LD50 value. To check the potency of the inoculum, a titration of the indicated test organism is carried out in control animals. The treatment group of animals is dosed with the test compound at 1 and 5 hours post-infection and observed for 7 days. The ED50 values are calculated using the mortality data collected. Results are indicated in the following table.

TABLE 2

| Route/Compound | ED$_{50}$ mg/kg/day | Confidence Limits |
| --- | --- | --- |
| Oral Administration: | | |
| Erythromycin A | 75.7 | 109.6-52.2 |
|  | 48.8 | 91.9-26.0 |
| 4''-O—TMS Ery A | 99.7 | 155.7-63.9 |
|  | 61.5 | 91.3-41.4 |
| 4'',11-bis-O—TMS-6-O—Me Ery A | 51.8 | 78.9-34.0 |
|  | 51.8 | 78.9-34.0 |
| 2'O—Ac—4'',11-bis-O—TMS Ery A | 250.* | — |
| 2',9-bis-O—TMS Ery A oxime | 150.* | — |
| Subcutaneous Administration: | | |

TABLE 2-continued

| Route/Compound | ED$_{50}$ mg/kg/day | Confidence Limits |
|---|---|---|
| Erythromycin A | 10.9 | 14.7–8.1 |
| 4″-O—TMS Ery A | 16.0 | 24.9–10.2 |
| 4″,11-bis-O—TMS-6-O—Me Ery A | 40.* | — |
| 2′-O—Ac—4″,11-bis-O—TMS Ery A | 40.* | — |
| 2′,9-bis-O—TMS Ery A oxime | 40.* | — |

*Highest level tested.

EXAMPLE 21

Extended mouse protection studies were performed to compare the compound of Examples 3 and 17, 2′-O-trimethylsilyl-6-O-methyl erythromycin A, with the parent compound and with erythromycin A in various oral dosage forms. The following results were obtained:

TABLE 3

| Vehicle/Compound | ED$_{50}$ mg/kg/day | Confidence Limits |
|---|---|---|
| 1. Strep. pyogenes | | |
| Phosphate buffer solution with milk* | | |
| 6-O—methyl ery A | 11.1 | 43.9–2.8 |
| 2′O—TMS-6-O—methyl ery A | 14.1 | 24.2–8.2 |
| Carboxymethylcellulose with milk* | | |
| 6-O—methyl ery A | 5.3 | 8.5–3.3 |
| 2′-O—TMS-6-O—methyl ery A | 7.8 | 13.8–4.4 |
| Phosphate buffer solution | | |
| Ery A | 37.2 | 53.9–25.6 |
| 6-O—methyl ery A | 5.9 | 11.0–3.1 |
| 2′-O—TMS-6-O—methyl ery A | 12.7 | — |
| 2. Staph. aureus | | |
| Phosphate buffer solution | | |
| Ery A | 75.7 | 109.6–52.2 |
| 6-O—methyl ery A | 27.2 | 36.7–20.2 |
| 2′-O—TMS-6-O—methyl ery A | 157.9 | 249.0–100.2 |
| Carboxymethylcellulose | | |
| Ery A | 86.0 | 130.9–56.5 |
| 6-O—methyl ery A | 25.0 | 32.0–19.5 |
| 2′-O—TMS-6-O—methyl ery A | 34.9 | 55.2–22.1 |
| 3. Strep. pneumoniae | | |
| Phosphate buffer solution | | |
| 6-O—methyl ery A | 1.6 | — |
| 2′O—TMS-6-O—methyl ery A | 9.3 | 14.2–6.1 |
| Phosphate buffer solution with milk* | | |
| 6-O—methyl ery A | 1.6 | — |
| 2′-O—TMS-6-O—methyl ery A | 10.9 | 22.9–5.2 |
| Carboxymethylcellulose | | |
| 6-O—methyl ery A | 2.4 | 3.7–1.6 |
| 2′-O—TMS-6-O—methyl ery A | 7.9 | 14.3–4.3 |
| Carboxymethylcellulose with milk* | | |
| 6-O—methyl ery A | 2.2 | 4.4–1.1 |
| 2′-O—TMS-6-O—methyl ery A | 7.3 | 14.2–3.7 |

*Reduces gastric acid secretion

EXAMPLE 22

Samples of 2′-trimethylsilylerythromycin A and 2′-trimethylsilyl-6-O-methylerythromycin A were dissolved in 10–50 ml dimethyl sulfoxide or acetonitrile to give a solution containing 15–75 mg/ml. An aliquot containing 75 mg of prodrug was added to aqueous buffers ranging in pH from 2 to 12 to give a final volume equal to 500 ml. The buffered mixtures were stirred at 37° C. for at least 90 minutes. A standard dissolution test apparatus (Vanderkamp 600, Van-Kel Industries, Inc., 36 Meridian Road, Edisoin, N.J. 08820) was used to provide temperature and stirring rate control.

Aliquots were taken at 15, 30, 45, 60, 90, 120, 180, 240 and 360 minutes for analysis. Each sample was mixed with an internal standard, adjusted rapidly to pH 9 with 1M tricine buffer and extracted immediately with ethyl acetate. The organic extracts were evaporated and redissolved in a solution of 3% tetrahydrofuran in heptane. Samples of these solutions were injected using an autosampler (WISP 71)B, Waters Chromatography, Division of Millipore, 34 Maple Street, Milford, Mass. 01757). The prodrugs and drugs were separated by high performance liquid chromatography, detected at 225 nm using a spectrophotometer (Spectroflow 773 Absorbence Detector, Kratos Analytical Instruments), and were quantified with a digital integrator.

The results indicated that 2′-trimethylsilylerythromycin A degraded to anhydroerythromycin A at pH 2 and 4. A very small amount of erythromycin A was detected at pH 6, accompanied by significant amounts of anhydroerythromycin. No erythromycin was formed at pH 8, 10 or 12. The possibility of enzymatic hydrolysis was not considered in this test; however, cleavage of one of the sugar moieties is the most likely route for enzymatic degradation, and such cleaveage would yield inactive products.

By comparison, the 2′-trimethylsilyl-6-O-methylerythromycin A was converted to the active drug 6-O-methylerythromycin A at acid pH. Very little or no conversion took place at pH 8 or above. The release rates at pH 5, 6 and 7 showed evidence of dissolution-rate limited release. The release rates at pH 3 and 4 showed evidence of both dissolution-rate limited release and also release from the initially dissolved material. The prodrug had little or no solubility (an important determinant of taste impact) at neutral or alkaline pH but was completely soluble (150 mg/L) at pH 2, which is the pH of stomach fluid in infants. These solubility properties severely restrict its decomposition at pH 7, which is highly desirable for good shelf life.

The foregoing is merely illustrative of this invention and is not intended to limit the invention to the compounds, compositions or methods of use specifically disclosed. Variations and changes which are evident to one skilled in the art are also encompassed by the invention as defined in the claims.

What is claimed is:

1. A relatively acid stable erythromycin A antibiotic having a plurality of hydroxyl groups, in which one or more of the hydroxyl groups are replaced by a group of the formula —O—SiR′R″R‴, where R′, R″, and R‴ are hydrogen or C$_1$ to C$_8$ alkyl, substituted alkyl, cycloalkyl, alkaryl or alkenyl, provided that R′, R″, and R‴ are not all hydrogen; and pharmaceutically acceptable salts and esters thereof.

2. A compound of the formula

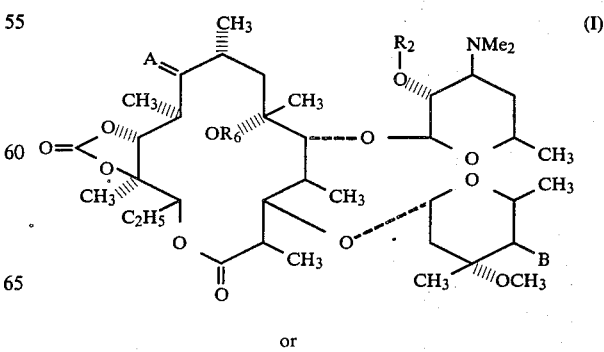

or

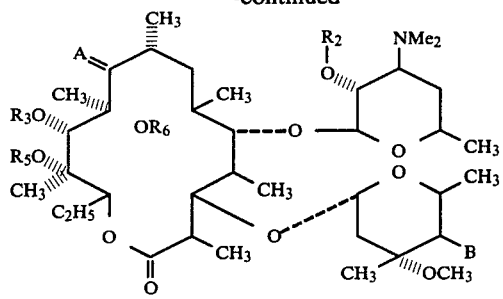

(II)

where
A is =O or =N—OR$_1$,
B is H or OR$_4$,
R$_1$, R$_2$, R$_3$, R$_4$ and R$_5$ are independently selected from hydrogen, C$_1$ to C$_8$ alkyl and SiR'R"R'", where R', R", and R'" are hydrogen or alkyl, substituted alkyl, cycloalkyl, alkaryl or alkenyl of 1 to 8 carbon atoms, provided that at least one of R', R", and R'" is not hydrogen; and
R$_6$ is selected from hydrogen, methyl, and ethyl; provided that at least one of R$_1$-R$_5$ is of the formula SiR'R"R'", and further provided that when A is =O and B is OH, at least one of R$_1$ to R$_6$ is neither hydrogen nor SiR'R"R'".

3. A compound according to formula (I) of claim 2 wherein R$_2$ is trimethylsilyl, A is =O, R$_6$ is hydrogen, and B is H or OR$_4$ where R$_4$ is C$_1$ to C$_8$ alkyl.

4. A compound according to formula (II) of claim 2 wherein A is =O, R$_2$ is trimethylsilyl, B is OH, and R$_6$ is methyl.

5. A compound according to claim 4 where A=O, R$_2$ is trimethylsilyl, B is OR$_4$, R$_3$-R$_5$ are all hydrogen, and R$_6$ is methyl.

6. A pharmaceutical composition in unit dosage form, comprising a therapeutically effective amount of a compound according to claim 1 in combination with a pharmaceutical carrier.

7. A liquid oral dosage form according to claim 6 wherein the pharmaceutical carrier comprises water, a sweetening agent, and a flavoring agent.

8. A method of treating and preventing bacterial infections in humans and lower animals in need of such treatment, comprising administering to the human or lower animal a therapeutically effective amount of the composition of claim 6.

* * * * *